US009050067B2

(12) United States Patent
Duncan et al.

(10) Patent No.: US 9,050,067 B2
(45) Date of Patent: Jun. 9, 2015

(54) PERCUTANEOUS NEPHROSTOMY PLUG DELIVERY DEVICE

(75) Inventors: Kate Duncan, Mooresville, IN (US); Gregory A. Frankland, Bloomington, IN (US)

(73) Assignee: Cook Medical Technologies, LLC, Bloomington, IN (US)

( * ) Notice: Subject to any disclaimer, the term of this patent is extended or adjusted under 35 U.S.C. 154(b) by 247 days.

(21) Appl. No.: 13/618,184

(22) Filed: Sep. 14, 2012

(65) Prior Publication Data

US 2013/0079812 A1    Mar. 28, 2013

Related U.S. Application Data

(60) Provisional application No. 61/539,114, filed on Sep. 26, 2011.

(51) Int. Cl.
*A61B 17/08*  (2006.01)
*A61B 17/00*  (2006.01)
*A61B 17/29*  (2006.01)

(52) U.S. Cl.
CPC ... *A61B 17/0057* (2013.01); *A61B 2017/00654* (2013.01); *A61B 2017/00898* (2013.01); *A61B 2017/2923* (2013.01)
USPC .................................................. 606/213

(58) Field of Classification Search
CPC ............... A61B 17/0057; A61B 2017/00637; A61B 2017/00654; A61B 2017/00659; A61B 2017/00004; A61B 2017/00898; A61B 2017/2923
USPC ........ 74/422, 89.17–89.19, 498–500; 604/57, 604/60, 61; 294/119.1, 207, 209; 606/213
See application file for complete search history.

(56) References Cited

U.S. PATENT DOCUMENTS 4,108,578 A  *  8/1978  Corey ........................... 417/331
4,744,364 A     5/1988  Kensey (Continued)

FOREIGN PATENT DOCUMENTS

WO    WO 93/08740       5/1993
WO    WO 2010/129042    11/2010

OTHER PUBLICATIONS

Samuel A. Giday et al., Novel Endoscopic Techniques Are Effective for Control of Hemorrhage During NOTES, Gastrointestinal Endoscopy, vol. 67, Issue 5, DDW abstract Issue 2008, Digestive Disease Week 2008, Apr. 2008, pp. AB113-AB114.

(Continued)

*Primary Examiner* — Amy R Weisberg
(74) *Attorney, Agent, or Firm* — Brinks Gilson & Lione

(57) ABSTRACT

A device for delivering a percutaneous nephrostomy plug is provided. The device comprises a tubular member configured for insertion into a biological body. The device further comprises a handle coupled to a proximal end of the tubular member. The handle comprises a pusher element, an actuation element, and a transmission. The pusher element is disposed within the tubular member, and is configured to deliver a plug through a distal end of the tubular member. The transmission is coupled to the tubular member and the actuation element, and the transmission is configured to cause a retraction of the tubular member relative to the pusher element in response to a depression of the actuation element. A first depression of the actuation element toward the tubular member urges a partial exposure of the plug. A second depression of the actuation element urges a further exposure of the plug.

4 Claims, 6 Drawing Sheets

(56) References Cited

U.S. PATENT DOCUMENTS

| | | | |
|---|---|---|---|
| 5,254,105 A | | 10/1993 | Haaga |
| 5,350,399 A | | 9/1994 | Erlebacher et al. |
| 5,437,631 A | | 8/1995 | Janzen |
| 5,540,715 A | | 7/1996 | Katsaros et al. |
| 5,938,668 A | * | 8/1999 | Scirica et al. ................ 606/145 |
| 5,993,460 A | * | 11/1999 | Beitelia et al. ............... 623/1.11 |
| 6,755,854 B2 | | 6/2004 | Gillick et al. |
| 6,860,895 B1 | * | 3/2005 | Akerfeldt et al. ............. 606/215 |
| 7,052,511 B2 | * | 5/2006 | Weldon et al. ................ 623/1.11 |
| 7,361,183 B2 | | 4/2008 | Ginn |
| 7,758,625 B2 | | 7/2010 | Wu et al. |
| 7,837,705 B2 | | 11/2010 | White et al. |
| RE44,297 E | * | 6/2013 | ÅKerfeldt et al. ............ 606/215 |
| 8,585,747 B2 | * | 11/2013 | Andreas et al. ............... 623/1.11 |
| 2004/0116904 A1 | | 6/2004 | Monga |
| 2005/0085856 A1 | | 4/2005 | Ginn |
| 2006/0100664 A1 | | 5/2006 | Pai et al. |
| 2007/0191768 A1 | | 8/2007 | Kolb |
| 2008/0091257 A1 | * | 4/2008 | Andreas et al. ............... 623/1.11 |
| 2009/0228037 A1 | | 9/2009 | Rego |
| 2009/0281507 A1 | | 11/2009 | Humphreys |
| 2009/0318955 A1 | | 12/2009 | Dave et al. |
| 2011/0077683 A1 | | 3/2011 | Huss |
| 2012/0089177 A1 | * | 4/2012 | Tegels ........................... 606/213 |
| 2014/0257459 A1 | * | 9/2014 | Masakazu .................... 623/1.11 |
| 2014/0343660 A1 | * | 11/2014 | Shimoyama ................. 623/1.11 |

OTHER PUBLICATIONS

Isaac Yi Kim et al., Effects of Commonly Used Hemostatic Agents on the Porcine Collecting System, Journal of Endourology, Jun. 2007, 21(6): 652-654.

Albert A. Mikhail et al., Use of Fibrin Glue in Percutaneous Nephrolithotomy, Urology, vol. 61, Issue 5, May 2003, pp. 910-914.

D. Lee, et al, Sealing Percutaneous Nephrolithotomy Tracts with Gelatin Matric Hemostatic Sealant: Initial Clinical Use, J Urol., Feb. 2004.

European Search Report for 12186181.9, 6 pages, dated Mar. 24, 2015.

* cited by examiner

PERCUTANEOUS NEPHROSTOMY PLUG DELIVERY DEVICE

CROSS REFERENCE TO RELATED APPLICATIONS

This application claims benefit under 35 U.S.C. §119(e) of U.S. provisional application 61/539,114, filed on Sep. 26, 2011, entitled "PERCUTANEOUS NEPHROSTOMY PLUG DELIVERY DEVICE," the content of which is incorporated herein by reference for all purposes.

TECHNICAL FIELD

This disclosure relates generally to medical devices and more particularly to devices for delivery of a nephrostomy plug to close a dilated nephrostomy tract in the kidney after a percutaneous nephrolithotomy procedure.

Percutaneous nephrolithotomy (PCNL) is a surgical procedure for removal or treatment of kidney stones through a small incision on the skin. Kidney stones are solid aggregations that form in the kidneys due to crystallization of minerals in the urine. Removal of kidney stones is necessary to relieve pain, bleeding or infections in the urinary tract due to blockages. During a PCNL procedure, the surgeon typically makes a small incision (1-1.5 cm) on the skin of the back of the patient. The surgeon then inserts a needle and a guide wire to create a nephrostomy tract in order to allow insertion of a nephroscope directly into the kidney. A nephroscope is a fiberoptic instrument that facilitates locating kidney stones and removing them through suction. In the case of large stones, an ultrasonic or laser probe may be inserted through the nephroscope to break the large tones into smaller pieces. After stone removal is complete, a nephrostomy tube is typically placed into the kidney and left in the patient for one or more days to drain urine. This may require the patient to stay in the hospital for one or more days for observation.

BRIEF SUMMARY

A first representative embodiment of the disclosure provides a medical device comprising a tubular member with a proximal end and a distal end, the tubular member is configured for insertion into a biological body. The medical device further comprises a handle coupled to the proximal end of the tubular member. The handle comprises a pusher element, an actuation element, and a transmission. The pusher element is disposed within the tubular member; the pusher element is configured to deliver a plug through the distal end of the tubular member. The transmission is coupled to the tubular member and the actuation element; the transmission is configured to cause a retraction of the tubular member relative to the pusher element in response to a depression of the actuation element. A first depression of the actuation element toward the tubular member urges a partial exposure of the plug. A second depression of the actuation element toward the tubular member urges a further exposure of the plug.

A second representative embodiment of the disclosure provides a medical device comprising a tubular member with a proximal end and a distal end, the tubular member is configured for insertion into a biological body. The medical device further comprises a handle coupled to the proximal end of the tubular member. The handle comprises a pusher element, and actuation element, and a transmission. The pusher element is configured to slide within the tubular member to deliver a plug through the distal end of the tubular member. The actuation element comprises a button and a spring coupled to the button. The transmission is coupled to the tubular member and the actuation element. The transmission comprises a first rack coupled to the button, a second rack coupled to the tubular member, a first gear engaged with the first rack, and a second gear engaged with the second rack. The second gear is selectively coupled to the first gear; and a roller clutch is coupled to the first gear. A first depression of the button urges a first rotation of the first and second gears in a first direction, causing a retraction of the tubular member relative to the pusher element. Upon release of the button, the first gear rotates in a direction opposite the first direction, but the second gear remains stationary. A second depression of the button urges a second rotation of the first and second gears in the first direction, causing a further retraction of the tubular member relative to the pusher element.

A third representative embodiment of the disclosure is a method for delivering a plug to a biological body. The method includes the step of inserting a distal end of a tubular member into a biological body, where the tubular member contains a plug at the distal end and a pusher element. The method further includes the step of causing a first retraction of the tubular member relative to the pusher element in a proximal direction, urging a partial exposure of the plug within the biological body. The method further includes the step of causing a second retraction of the tubular member relative to the pusher element in a proximal direction, urging a further exposure of the plug within the biological body.

Advantages of the present disclosure will become more apparent to those skilled in the art from the following description of the preferred embodiments of the disclosure that have been shown and described by way of illustration. As will be realized, the disclosed subject matter is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Turning now to FIGS. 1-5, a device 10 for delivering a nephrostomy plug to a kidney is provided. The device 10 is configured to receive, enclose, and deliver a small plug to be inserted into the kidney to close a nephrostomy tract left in a patient after a PCNL procedure. The device 10 is also configured to allow the user to deploy the plug in a stepwise fashion to control the location and rate of deployment. The device 10 further is configured to be operated in conjunction with a nephroscope using direct vision or fluoroscopy.

Figure 1:
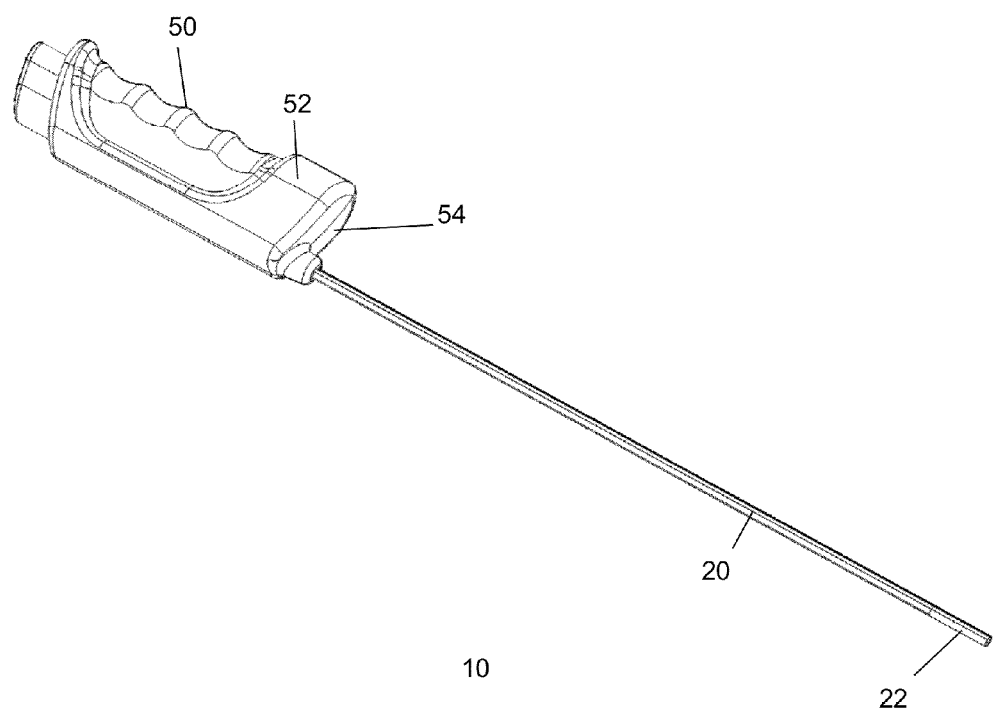
FIG. 1 is a perspective view of a device for percutaneous delivery of a nephrostomy plug to the kidney.
Figure 2:
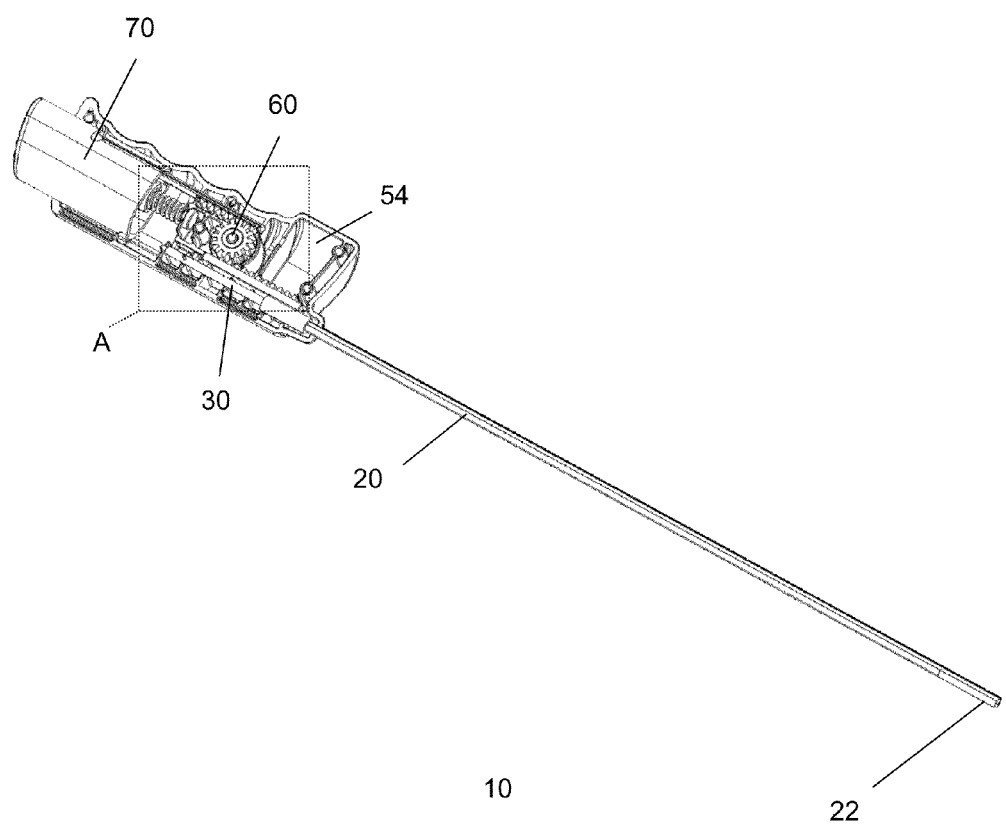
FIG. 2 is a perspective view of the device of FIG. 1 with the top half of the handle housing removed to show the mechanism inside.

Referring to FIG. 1, the device 10 includes an elongate sheath 20 that may be slidably disposed over a push rod 30 (shown in FIG. 2). The sheath 20 may be an elongated tube made of a moldable plastic material such as polyethylene teraphthalate (PET). In a preferred embodiment, the sheath 20 may have an outer diameter of about 12 Fr (4 mm), an inner diameter of about 10.6 Fr (3.53 mm), and a working length of about 37 cm. The diameter of the sheath 20 is designed to be compatible with the typical 12-Fr (4 mm) working channel of a nephroscope. The push rod 30 may be a solid thin cylindrical bar made of 304 SS stainless steel or similar, for example. In a preferred embodiment, the push rod 30 may have a working length of about 34.5 cm and a diameter of about 3.175 mm.

The device 10 also includes a handle 50 a shown in FIG. 1. The handle 50 may be ergonomically designed to make the device intuitive and comfortable to use through a nephroscope. The handle 50 may be made of molded acrylonitrile butadiene styrene (ABS) plastic or similar moldable plastic materials. The handle may include a bottom handle half 52 and a top handle half 54. The handle 50 may enclose a transmission mechanism 60, as shown in FIG. 2. The handle may also include a push-button 70.

Figure 2A:
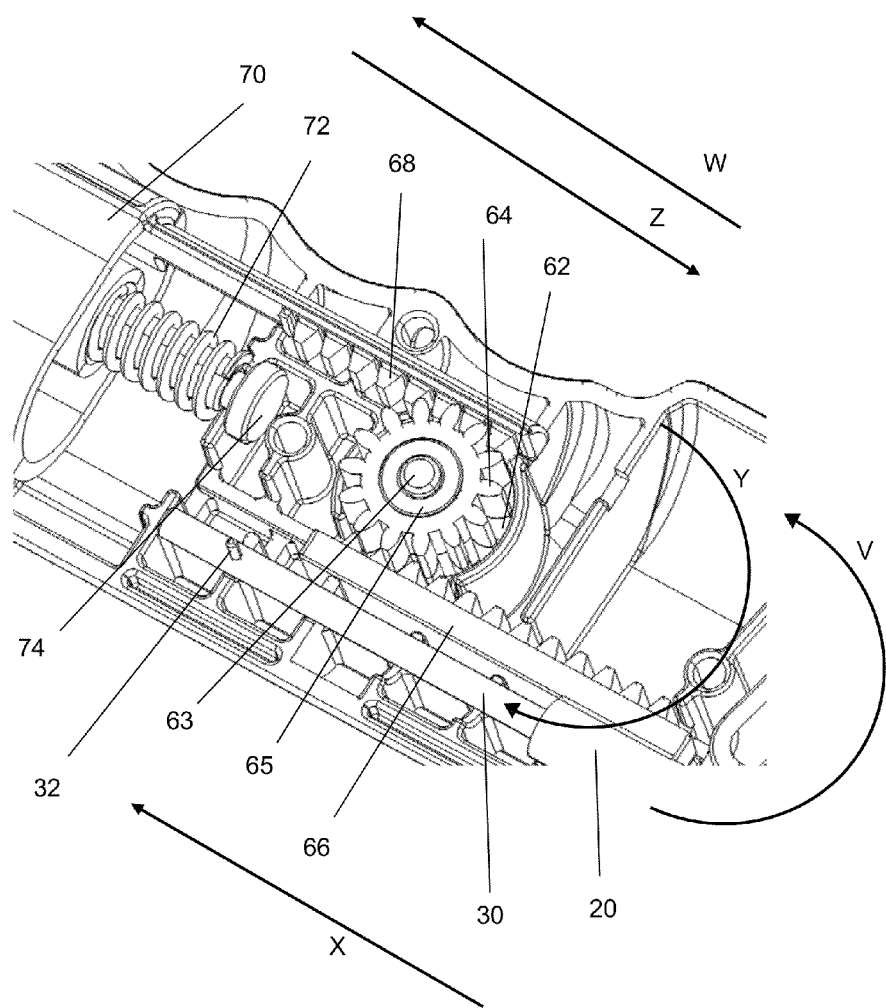
FIG. 2A is a close-up view of detail A of FIG. 2.

Referring to FIG. 2A, the transmission mechanism 60 may include a bottom spur gear 62, a top spur gear 64, a bottom rack gear 66, and a top rack gear 68. The spur gears 62, 64, rack gears 66, 68 and push-button 70 may be made of molded polyethylene terepthalate glycol (PETG) plastic or similar moldable plastic materials.

In one embodiment, the sheath 20 may be coupled to bottom rack gear 66 as shown in FIG. 2A. The sheath 20 may be extruded and then insert molded into bottom rack gear 66, for example. Bottom rack gear 66 may then be placed on the bottom handle half 52. The top rack gear 68 may be coupled to the push button 70 and also placed on the bottom handle half 52. A spring 72 may be inserted into the push button 70 and coupled to a pin 74, the pin 74 coupling the push button 70 to the bottom handle half 52. The push rod 30 may be inserted into the bottom handle 52 and fixed to it by, for example, a pin 32.

Figure 3:
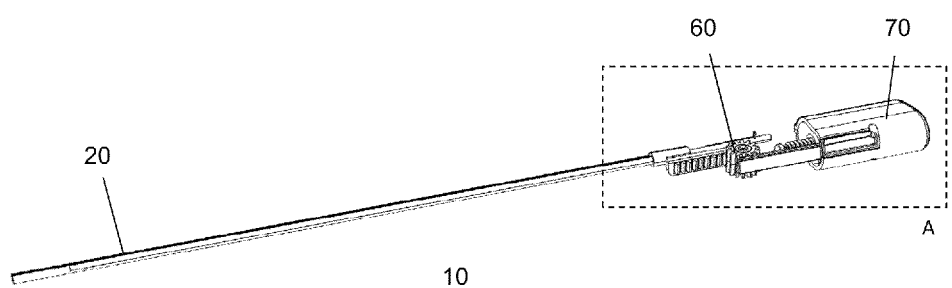
FIG. 3 is a perspective view of the device of FIG. 1 with the handle housing removed.
Figure 3A:
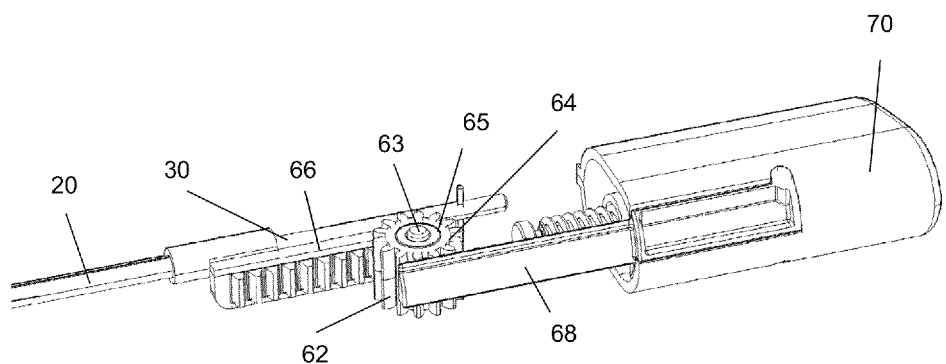
FIG. 3A is a close-up view of detail A of FIG. 3.

A hub or pin 63 may be inserted into the bottom spur gear 62. The hub 63 may be a stainless steel hub, for example. A roller clutch 65 may be press fit into the top spur gear 64. Then the spur gears 62, 64 may be selectively coupled together by inserting the hub 63 into the roller clutch 65. The bottom spur gear 62 may then be coupled with the bottom rack gear 66, and the top spur gear 64 may be coupled to the top rack gear 68, as shown in FIG. 2A. This can also be appreciated with reference to FIGS. 3 and 3A, which show a different perspective (without the handle 50 housing) of the transmission mechanism 60 coupled to the sheath 20 and the push-button 70.

Figure 4:
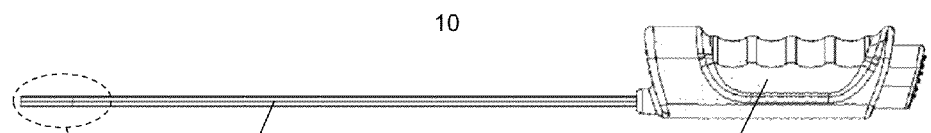
FIG. 4 is another perspective view of the device of FIG. 1.

FIG. 4 illustrates the device 10 loaded with a nephrostomy plug 80 at the distal end 22 of the sheath 20. In some embodiments, the nephrostomy plug 80 may be made of collagenous extracellular matrix (ECM) or other collagenous materials that have been subjected to processes that expand the materials. Suitable collagenous or ECM materials can be prepared, for example, as described in U.S. Patent Publication No. 20090326577, published Dec. 31, 2009, and U.S. Patent Publication 2009/0318934, published Dec. 24, 2009, hereby incorporated by reference in their entirety. Expanded remodelable collagenous materials can be provided in any suitable form, including a flowable aqueous composition (e.g., a fluidized composition), a powder, a gel, a sponge, foam, one or more sheets, or a cast body.

In certain forms, such expanded materials can be formed by the controlled contact of an ECM material with one or more alkaline substances until the material expands, and the isolation of the expanded material. Any suitable alkaline substance generally known in the art can be used in this regard. Suitable alkaline substances can include, for example, salts or other compounds that that provide hydroxide ions in an aqueous medium. Preferably, the alkaline substance comprises sodium hydroxide (NaOH). Illustratively, the contacting with an alkaline substance can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried construct formed with the expanded ECM material can be highly compressible (or expandable) such that the material can be compressed for delivery, such as from within the lumen of a cannulated delivery device, and thereafter expand upon deployment from the device, for example, so as to become anchored within a patient or otherwise occupy a space within a patient such as when closing or filling an opening or passageway in the patient.

Alkaline treatment of the material can cause changes in the physical structure of the material that in turn cause it to expand. Such changes may include denaturation of the collagen in the material. Denaturation of the collagen matrix of the material can be observed as a change in the collagen packing characteristics of the material, for example a substantial disruption of a tightly bound collagenous network of the starting material. Consequently, an expanded collagenous material typically appears more porous than a corresponding non-expanded collagenous material. The more foamy and porous structure of an expanded ECM or other collagenous material can allow the material to be cast or otherwise prepared into a variety of sponge or foam shapes for us in the preparation of medical materials and devices. It can further allow for the preparation of constructs that are highly compressible and which expand after compression. Such properties can be useful, for example, in preparing the plug to be compressed and loaded into the delivery device described herein. Thus in some embodiments, a plug 80 of cylindrical shape may be used in conjunction with the device 10. In a preferred embodiment, the plug 80 may have a circular cross-section of about 0.2 inches, and a length of about 0.8-0.9 inches. Once within the body, the plug 80 may hydrate and expand to a size of about 0.6-0.7 inches in diameter in order to fill a nephrostomy tract in the kidney caused by the percutaneous nephrolithotomy procedure.

A starting ECM material (i.e. prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In some instances, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated by reference in its entirety, containing these components can be prepared and applied to an expanded collagenous material. Other means for returning or introducing bioactive components to an expanded remodelable collagenous material include spraying, impregnating, dipping, etc. as known in the art.

In addition or as an alternative to the inclusion of native bioactive components, such as those provided in a submucosa or other ECM extract, non-native bioactive components including those synthetically produced by recombinant technology or other methods, may be incorporated into the expanded remodelable collagenous material. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the expanded remodelable collagenous materials include, for example, antibiotics, thrombus-promoting substances such as blood clotting factors, e.g. thrombin, fibrinogen, and the like. As with the bioactive components previously described, these substances may be applied to the expanded remodelable collagenous material as a premanufactured step, immediately prior to the procedure (e.g. by soaking the material in a solution containing a suitable antibiotic such as cefazolin), or during or after engraftment of the material in the patient.

Figure 4A:
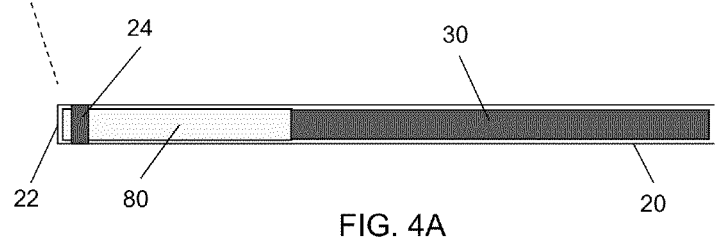
FIG. 4A is a close-up view of detail A of FIG. 4 showing the plug loaded into the device.
Figure 4B:
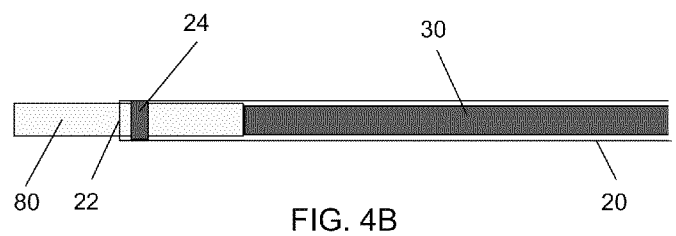
FIG. 4B is a close-up view of detail A of FIG. 4 showing the plug halfway deployed.
Figure 4C:
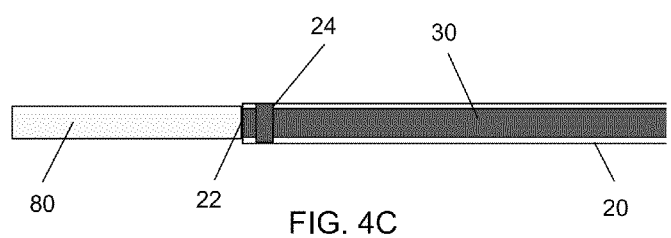
FIG. 4C is a close-up view of detail A of FIG. 4 showing the plug fully deployed.

FIGS. 4 and 4A illustrate the device 10 loaded with the plug 80. To operate the device 10, the user may insert the distal tip 22 of the device 10 through the working channel of a nephroscope that has already been inserted into the patient's kidney during a PCNL procedure. The device 10 may be operated in conjunction with a nephroscope using direct vision or fluoroscopy. The sheath 20 may include a radiopaque band 24 at its distal end 22 as shown in FIGS. 4A-4C. The radiopaque band 24 may help to identify the precise location of the sheath's distal end 22 for positioning accuracy.

Once the device 10 is in position, the user may depress the push-button 70 once. The depression of the push-button 70 may cause a translational movement of the top rack gear 68 in direction Z, as illustrated in FIG. 2A. The movement of rack gear 68 may in turn cause the spur gears 62, 64 to rotate in direction Y, which results in a translational movement of rack gear 66 in direction X. The movement of rack gear 66 in direction X may thus urge a corresponding retraction of sheath 20 in the same direction. Since the push rod 30 remains in a fixed position relative to the handle 50, the retraction of the sheath 20 may cause a partial exposure of the plug 80. In some embodiments, one depression of the push-button 70 may cause about half the plug 80 to be exposed, as illustrated in FIG. 4B. The portion of the plug 80 deployed halfway may expand in size within the kidney as a result of hydration.

Next the user may withdraw pressure on the push-button 70. The spring 72 may cause the push-button 70 to return to its original position after pressure has been withdrawn. As a result of the push-button 70 returning to its original undepressed position, the top rack gear 68 may move in direction W, causing rotation of top spur gear 64 in direction V. The bottom spur gear 62 however may remain in position as a result of the roller clutch 65 preventing transmission of rotation from the top spur gear 64 along with the rotation of the lower spur gear 62 in the V direction. This, in turn, ensures that the sheath 20 remains retracted relative to the push rod 30 as the push-button 70 returns to its original undepressed position.

Figure 5:
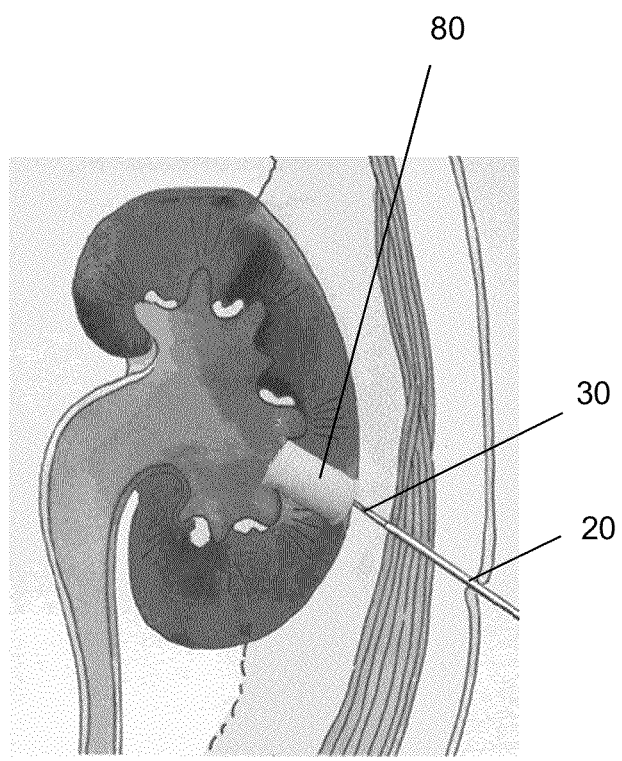
FIG. 5 is an illustration of the method of operation of the device of FIG. 1.

The user next may depress the push-button 70 once again, repeating the translational motion of the top rack gear 68, which may cause both the top spur gear 64 and the bottom spur gear 62 to rotate in direction x. This, in turn, may cause the bottom rack gear 66 to further move in direction b, which may cause the sheath 20 to further retract in direction b relative to the handle 50 and push rod 30. As a result, the plug 80 may be further exposed as illustrated in FIG. 4C. In some embodiments, a further exposure of plug 80 may also result in full release of the plug into the body of the patient. The plug 80 may then be able to expand to full size due to hydration, providing a seal of the nephrostomy tract on the kidney. FIG. 5 illustrates one embodiment of device 10 inserted into a patient's kidney after plug 80 is fully released into the kidney to provide a seal. It may be appreciated that, in other embodiments, the second depression of the push-button 70 causes only an additional partial deployment of the plug 80. The total deployment of the plug 80 may occur at the end of a total of three, or more, depressions of the push-button 70.

It should be appreciated that the device 10 may be operated using a single hand, thus freeing the user to manipulate any other instrument with the other hand. In addition, the handle 50 may be ergonomically designed for intuitive use and comfort. In addition, the stepwise advancement or exposure of the plug permits the user to control the location and the rate of deployment for effectively.

While the preferred embodiments of the disclosure have been described, it should be understood that the disclosure is not so limited and modifications may be made without departing from the disclosure. The scope of the invention is defined by the appended claims, and all devices that come within the meaning of the claims, either literally or by equivalence, are intended to be embraced therein.

The invention claimed is:
1. A medical device, comprising:
a tubular member having a proximal end and a distal end, the tubular member configured for insertion into a biological body;
a handle coupled to the proximal end of the tubular member, the handle comprising:
a pusher element configured to slide within the tubular member to deliver a plug through the distal end of the tubular member;
an actuation element comprising:
a button; and
a spring coupled to the button;
a transmission coupled to the tubular member and the actuation element, the transmission comprising:
a first rack coupled to the button;
a second rack coupled to tubular member;
a first gear engaged with the first rack;
a second gear engaged with the second rack, the second gear selectively coupled to the first gear; and
a roller clutch coupled to the first gear;
wherein a first depression of the button urges a first rotation of the first and second gears in a first direction, causing a retraction of the tubular member relative to the pusher element;

wherein upon a release of the button the first gear rotates in a direction opposite the first direction but the second gear remains stationary; and wherein a second depression of the button urges a second rotation of the first and second gears in the first direction, causing a further retraction of the tubular member relative to the pusher element.

2. The medical device of claim 1, wherein the pusher element is a cylindrical rod.

3. The medical device of claim 1, further comprising the plug disposed within the tubular member at the distal end of the tubular member.

4. The medical device of claim 3, wherein the plug has a cylindrical shape.

* * * * *